United States Patent [19]
Chandraratna et al.

[11] Patent Number: 5,505,088
[45] Date of Patent: Apr. 9, 1996

[54] ULTRASOUND MICROSCOPE FOR IMAGING LIVING TISSUES

[75] Inventors: P. Anthony N. Chandraratna, Rancho Palos Verdes; Roger A. Stern, Cupertino, both of Calif.

[73] Assignee: Stellartech Research Corp., Mountain View, Calif.; a part interest

[21] Appl. No.: 102,613

[22] Filed: Aug. 27, 1993

[51] Int. Cl.⁶ .............................. G01N 29/04; A61B 5/04
[52] U.S. Cl. ............... 73/623; 128/662.05; 128/662.06
[58] Field of Search ................... 128/662.06, 662.03, 128/662.05; 73/606, 618, 623

[56] References Cited

U.S. PATENT DOCUMENTS

| | | | |
|---|---|---|---|
| 4,546,771 | 10/1985 | Eggleton et al. | 128/660 |
| 4,862,893 | 9/1989 | Martinelli | 128/662.03 |
| 4,869,258 | 9/1989 | Hetz | 128/660.10 |
| 4,886,059 | 12/1989 | Weber | 128/662.06 |
| 4,917,097 | 4/1990 | Proudian et al. | 128/662.06 |
| 4,930,515 | 6/1990 | Terwilliger | 128/662.06 |
| 4,967,752 | 11/1990 | Blumenthal et al. | 128/660.1 |
| 5,158,088 | 10/1992 | Nelson et al. | 128/662.05 |
| 5,354,220 | 10/1994 | Ganguly et al. | 128/662.06 |
| 5,372,138 | 12/1994 | Crowley et al. | 128/662.06 |
| 5,373,845 | 12/1994 | Gardineer et al. | 128/662.06 |

*Primary Examiner*—Richard Chilcot
*Assistant Examiner*—Max H. Noori
*Attorney, Agent, or Firm*—Eppa Hite

[57] ABSTRACT

A series of devices for in vivo imaging of cellular architecture in a variety of tissues. A 200 MHz transducer is mounted on the tip of a cardiac catheter, gastroscope, colonoscope, bronchoscope, laparoscope or similar device, where it is moved mechanically to produce B-mode images of cells in the tissue. The ultrasound beam is focused in a subsurface region of tissue, and ultrasound which is backscattered from the focal zone is analyzed to produce images. Because heart motion may interfere with cardiac imaging, images are gated in mid-diastole for cardiac applications.

15 Claims, 5 Drawing Sheets

ULTRASOUND MICROSCOPE FOR IMAGING LIVING TISSUES

BACKGROUND OF THE INVENTION

1. Technical Field

The present invention relates generally to ultrasound visualization techniques and more particularly to catheter or endoscope based ultrasound microscopes.

2. Prior Art

Conventional catheters have been designed with ultrasound transducers operating at between 5 and 30 MHz which are introduced inside the bodies of patients. These low frequencies of ultrasound can create images to depths of several centimeters inside tissues. For a given transducer diameter, the axial resolution of an ultrasound beam increases as the frequency increases. The beam resolution along its axis is increased when pulse duration is decreased, by transmitting a pulse with increased bandwidth. Transducer diameter, frequency, bandwidth and sensitivity must be optimized simultaneously when designing ultrasound transducers.

Conventionally, 2.25 or 3.0 MHz transducers are used to image cardiac structures such as the mitral, tricuspid and aortic valves and left ventricular walls. Transducers operating at 5 MHz placed on infants and childrens bodies provide better resolution, although the beam penetration depth is less than with lower frequencies. Transducers operating at 5 or 7.5 MHz can image superficial structures such as the carotid and femoral arteries. Transesophageal echocardiography utilizes 5 or 7.5 MHz transducers with considerably improved image quality due to the higher frequencies and shorter distances from the transducer to the heart. Higher 20 to 30 MHz frequency transducers have been mounted on the tips of cardiac catheters for intravascular imaging, and have provided excellent resolution of the intima, media and adventitia of arterial walls. Transducers operating at 2 to 30 MHz frequencies provide excellent images of the heart and other organs, but still cannot image cellular detail.

When transducer frequency is increased to 1000 MHz, the ultrasound wavelength is significantly decreased and approaches that of light. The image resolution achievable with ultrasound at 1000 MHz is approximately 1 to 1.5 microns, which enables imaging cellular detail. Transducers operating at 600 to 1000 MHz can accurately assess myocardial cellular detail.

Prior art has imaged cellular characteristics in thin (5 micron) sections of tissue. Myocardial pathology, which is characterized by myocyte necrosis, lymphocytic infiltration and interstitial fibrosis, can be visualized clearly with very high frequency ultrasound. However, ultrasound in the very high frequency range trades off the disadvantage of very shallow penetration into tissue.

U.S. Pat. No. 4,546,771 by Eggleton et al. discloses a biopsy needle for positioning an ultrasound transducer capable of producing and receiving high (100 to 500 MHz) frequency ultrasound. Passing the needle into tissues enables microscopic examination of tissues within living bodies. Inside the needle a transducer generates an ultrasonic beam which is directed axially, then reflected off a mirror located at 45° in the needle to be directed radially from the needle and focused at a point in the tissue. The tissue backscatters ultrasound toward the needle, where the 45° mirror reflects it up along the needle axis to be received by the transducer. A piezoelectric bimorph actuator can reciprocate the mirror along the needle axis to produce a sequence of parallel A-scans, for forming a B-scan in a plane parallel to the needle axis. A second embodiment utilizing a rotary actuator can oscillate the mirror around the needle axis. This produces a sequence of radial A-scans for forming a B-scan in a plane perpendicular to the needle axis. Eggleton emphasizes frequencies between 400 and 500 MHz.

In the inventors experience, 400 MHz or higher frequency transducers are not satisfactory for imaging cells in thick-sample sections of tissue. This is due to the extremely shallow depth of penetration of ultrasound at such high frequencies. In-vivo ultrasonic imaging of details of cells from thick sections is not known to have been reported.

SUMMARY OF THE INVENTION

It is an object of the present invention to provide an ultrasound microscope means for imaging living tissues with resolution sufficient to visualize individual cells.

It is another object to visualize individual cells in-vivo using minimally invasive means.

It is a further object to provide ultrasound microscope means for imaging forward from the tip of a catheter.

It is an additional object to provide ultrasonic microscopes incorporated into various devices such as cardiac catheters, hysteroscopes, colonoscopes, gastroscopes, bronchoscopes, laparoscopes or in surface imaging devices.

The present invention is an ultrasonic microscope which operates at a frequency substantially above those of conventional ultrasound imaging devices and substantially below those of conventional ultrasound microscopes, preferably around 200 MHz. The microscope comprises catheter means having a body with inside and outside surfaces ending with a distal tip, and a long axis. A pivot means mounts a transducer means around a pivot axis normal to the long axis, onto the inside surface adjacent to the tip of the catheter. An ultrasound transducer assembly is positioned pivotally on the pivot means. The transducer transmits and receives high frequency ultrasound in beams for A-scan lines in a plane which includes the long axis. An actuator reciprocates the transducer to scan the ultrasound beams at increasing angles along an arc across a B-scan sector in the plane. Conductors provide ultrasound energy for the transducer and power for the actuator which are disposed inside the catheter. A controller controls the electrical energy flowing through respective conductors to the transducer and to the actuator.

Among the advantages of the invention are that scanning forward from a catheter enables a transducer to look ahead to and to approach, at an angle to surfaces to be imaged. Another advantage is that it allows imaging without penetrating the tissues.

These and other features of the invention will become more apparent through reference to the accompanying Detailed Description and Drawing.

DETAILED DESCRIPTION OF THE INVENTION

For potential in vivo applications, lower frequency ultrasound transducers can provide deeper penetration in tissue, but ultrasonic microscopy development has lacked a demonstration that lower frequency transducers could reliably detect cellular abnormalities. The present invention establishes minimum frequencies necessary for cellular imaging.

Cardiac cell detail, including normal cardiac myocytes and pathological phenomenon such as interstitial fibrosis, cell fallout and round cell infiltration, can be clearly identified in thin (5 μm) sections of tissue by using 1000, 600, 400 or 200 MHz transducers. However, backscatter images of cells within thick sections cannot be obtained using 600 or 400 MHz transducers due to their inadequate tissue penetration and the weakness of backscattered signals. At the lower end of the range of potential usable frequencies, with 100 MHz transducers having inadequate resolution cellular imaging is not practical.

The invention teaches the feasibility of using a 200 MHz transducer for backscatter imaging of cells from full thickness subsurface layers of myocardium. After ultrasonic imaging experiments, myocardial tissue was sectioned in 5 micron thick sections parallel to the imaging plane, stained with hematoxylin and eosin, and then examined by light microscopy. The diameters of cells measured by high frequency ultrasound were similar to those of cells measured by light microscopy. The ultrasound images of cardiac myocytes were comparable to the light microscope images.

Figure 1:
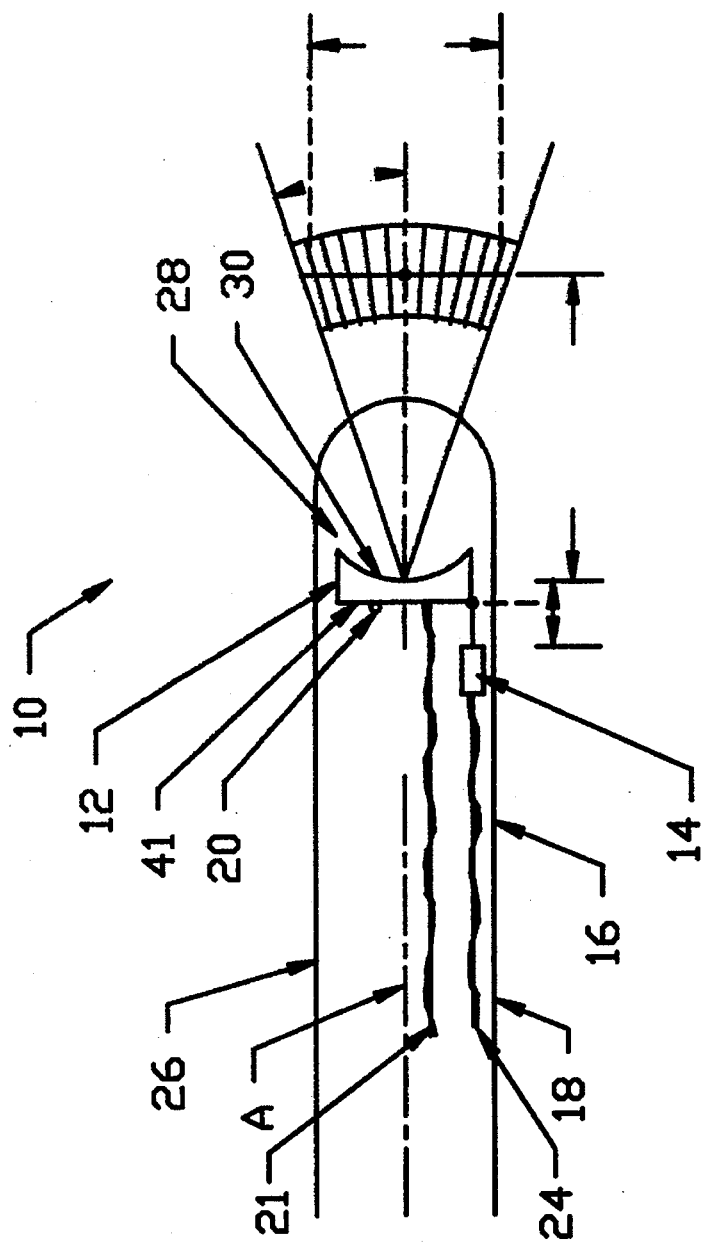
FIG. 1 is a cross-section along the long axis through a catheter tube, its distal tip, an ultrasound transducer and an actuator, and shows a sequence of radial A-scan lines forming a B-scan sector, according to the invention.

Referring to FIG. 1, in the present invention an ultrasonic microscope 10 comprises a catheter-type delivery means 18 with a distal tip 16, and generic pivot means 20 for mounting ultrasound transducer 12 to be scanned with a mechanical linear actuator 14. Transducer and actuator control signals are supplied through electrical conductors 21 and 24 within the catheter tube 26. Transducer 12 transmits an ultrasonic beam through an acoustic lens 28 having a concave surface 30 which focuses the ultrasound to a focal point in the tissue. Alternatively, transducer surface 30 can be concave to focus the ultrasound. Pointing transducer 12 determines the direction of the beam. Where transducer 12 points along axis A through tip 16, it focuses at the nominal focal point (NFP). The focal point is deflected from the NFP as the transducer direction is changed.

The ultrasound beam has a Near Field depth $NF=d^2/\lambda$ where d (=2 mm) is the transducer 12 diameter and $\lambda=c/f$ ($\cong 7$ μm @200 MHz) is the ultrasound wavelength.

Transducer 12 having diameter d=2 mm and frequency f=200 MHz projects transmit beam T which is collimated through possibly 10 cm of depth. This is farther than the nominal focal point depth, which is constrained by the penetration of ultrasound at 200 MHz. An appropriate lens 28 or surface 30 curvature focuses the beam for maximum resolution focal spot size. The focal spot pixel diameter can be as narrow as 7 μm. Its resolution is a diffraction limited function of transducer diameter d (preferably 2 mm), focal length FL (preferably 3 mm) and frequency f (preferably 200 MHz).

The pixel length or axial depth resolution varies directly with the bandwidth (inversely with the pulse duration of ultrasound). It is $\cong 7$ μm for a bandwidth of 200 MHz. Shorter pulses require higher bandwidths.

In microscope operation, an ultrasonic pulse centered at a frequency of preferably $\cong 200$ MHz is transmitted into the tissue (not shown) around the tip. The ultrasonic signal's resulting backscatter is next received, amplified and envelope-detected, to form individual A-scan lines. The ultrasound beam is mechanically scanned orthogonally to its axis, which moves across a B-scan sector through an arc around a pivot axis. The pivot axis is perpendicular to but does not necessarily intersect the long axis A of the catheter 18. A-scan lines radially at incremental angles together form a B-scan. For example, two hundred A-scans spaced angularly at 0.05 degrees together form a sector 10.0° wide. At an NFP of 2.0 mm, the separation between A-line pixels is 1.7 microns. The time to receive backscatter signals from each A-line is under 5 microseconds. A thirty frame-per-second rate allows 166 microseconds per radial A-scan, which is substantially greater than the time required to acquire data from an individual A-scan line.

Figure 2:
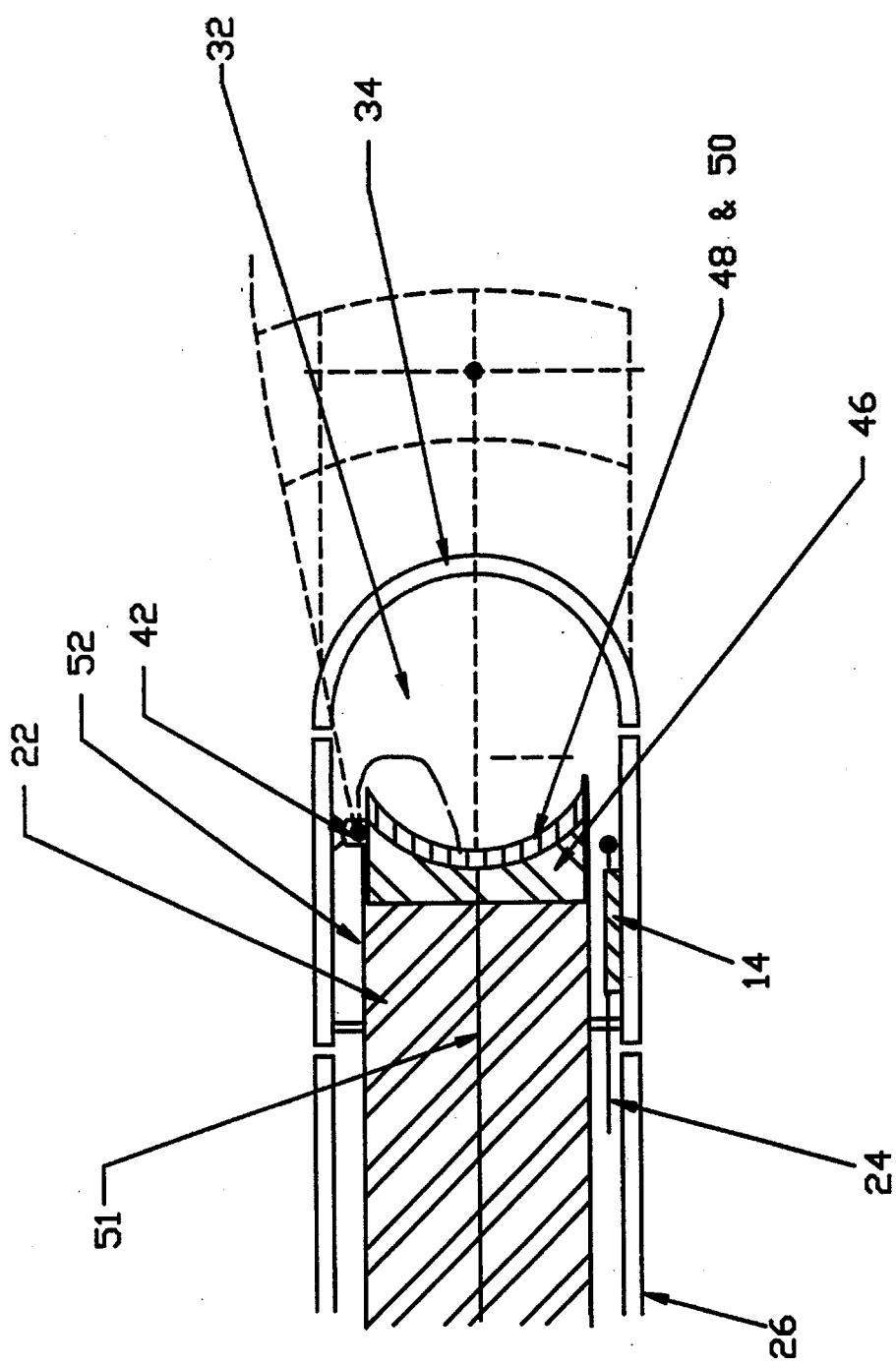
FIG. 2 shows the invention in a first embodiment with its pivot means as a peripheral hinge.

FIG. 2 shows the invention in a first embodiment having an outer catheter body 26 containing coaxial cable connections 22 for electrical signals to transducer 12, and containing drive conductors 24 for energizing a scanning-actuator means 14 such as a piezo-bimorph. Outer catheter body 26 terminating tip 16 contains ultrasound transducer 12 and coupling fluid 32 for transmitting ultrasonic energy to the end of catheter 18. Catheter tip 16 has acoustic window 34 which passes ultrasound into the tissue, and admits energy backscattered from the tissue, as data to be received by transducer means 12.

Transducer 12 is mounted on a pivot means or rotational joint in the form of a peripheral hinge 42 which allows scanning actuator means 14 to move transducer 12 for performing a B-mode scan.

Transducer 12 as shown in FIG. 2 is fabricated by a backing material 46 attached to the end of coaxial cable 22, and curved to focus ultrasonic energy at a desired point inside tissue. A piezoelectric film 48 of for example polyvinylidene fluoride PVDF on both sides has applied metallization 50 which conforms to shaped backing material 46. Alternatively, a transducer 12 could be embodied using zinc oxide, lithium niobate or PZT, on a lens of sapphire or quartz. The coaxial cable 22 center conductor 51 pierces backing material 46 and forms an electrical contact with back metallization 50 on piezoelectric film 48. The coaxial cable 22 outer shield conductor 52 extends over shaped backing material 46 and forms an electrical contact with front metallization 50.

A linear actuator 14 is attached to one outer edge of the transducer assembly 12, and is in turn secured to the inside of catheter body 26. A rotational joint 42 pivot means is attached to the opposite edge of transducer assembly 12. When the attached electrical drive conductors 24 energize actuator 14, this rotates transducer assembly 12 to perform a B-scan. The FIG. 3 embodiment has the advantage of integrating the coaxial cable 22 and the transducer assembly 12, and minimizes potential electrical impedance mismatch.

Figure 3:
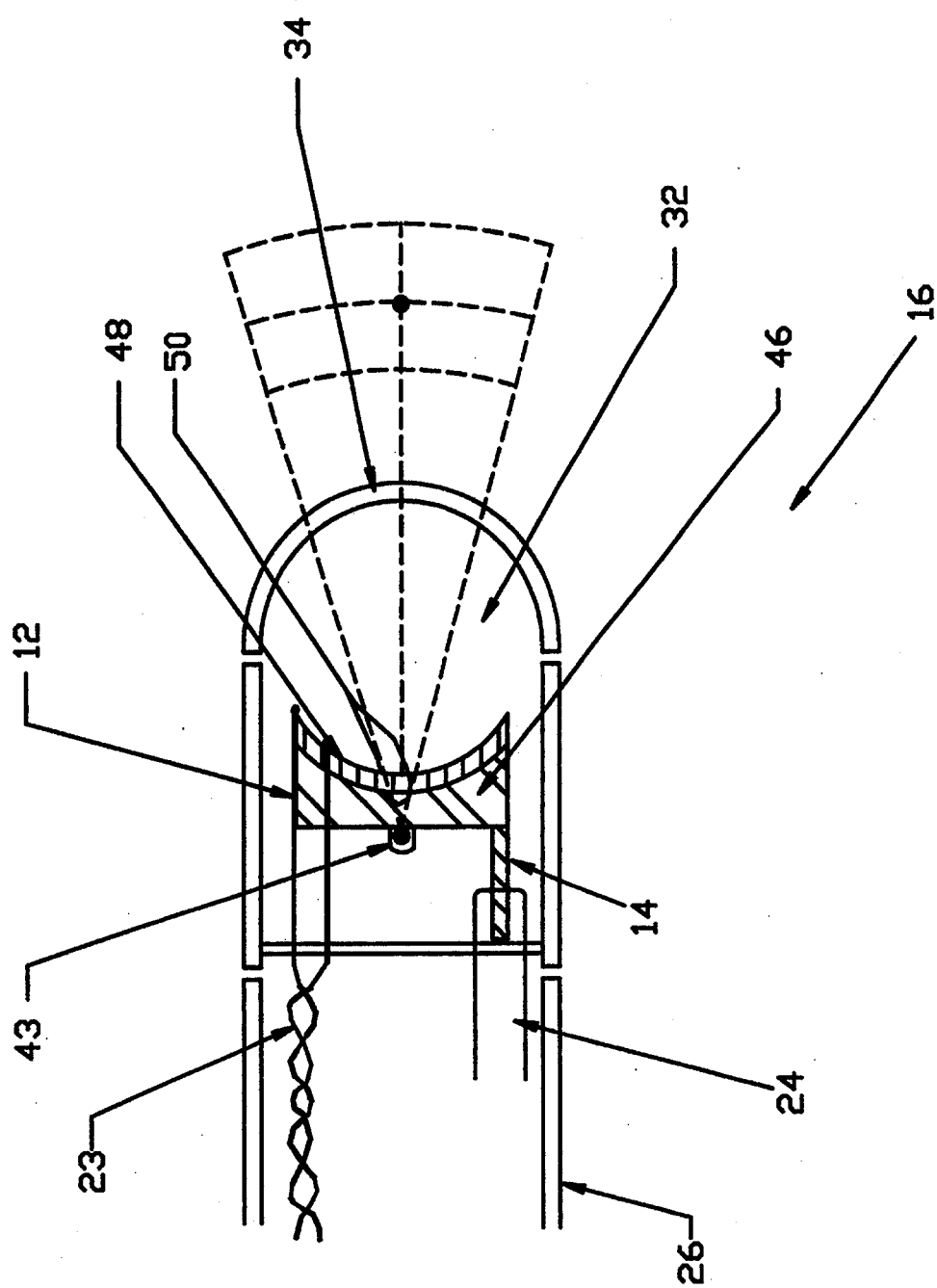
FIG. 3 is a cross-section through a second embodiment with its pivot means as a central ball joint.

FIG. 3 shows the invention in an alternate embodiment which has outer catheter body 26 containing wires as twisted pair 23 connections for electrical signals to transducer 12.

Body 26 also contains drive conductors 24 for powering scanning actuator means 14. The outer catheter body 26 terminating tip 16 contains ultrasound transducer 12 and coupling fluid 32 to transmit ultrasonic energy to the end of the catheter. The catheter tip 16 contains acoustic window 34 which transmits ultrasound into the tissue, and receives energy backscattered from the tissue. Transducer 12 is mounted on a centrally located rotational or ball type joint 43 allowing scanning means 14 to move the transducer 12 to perform a B-mode scan.

Transducer 12 as shown in FIG. 3 is embodied by a backing material 46 curved to focus ultrasonic energy. A piezoelectric film 48 of for example PVDF has applied metallization 50 on both sides conforming to shaped backing material 46. One of the signal conductor wires of twisted pair 23 electrically contacts back metallization 50 of piezoelectric film 48. The other wire of pair 23 electrically contacts front metallization 50.

A linear actuator 14 is attached to an edge on the outside of transducer assembly 12 and is in turn secured to the inside of catheter body 26. Pivot means in the form of a rotational joint 43 is centered at the back of backing material 46. When electrical drive conductors 24 energize actuator 14 this rotates transducer assembly 12 to perform a B-scan.

A central rotational joint 43 in the form of a ball joint allows two degrees of rotational freedom. Then, a second linear actuator (not shown) can be located 90° around the rim from first actuator 14. This allows selecting B-scan sector plane orientations at any desired angle around long axis A of catheter 18. B-scans taken at multiple angles allow scanning conical volumes diverging out axis A. Such image-scan data can be time-filtered to form C-scan slices in any plane within the conical volume. Other processes, including 3D displays, can be practiced on such image scan data.

Figure 4:
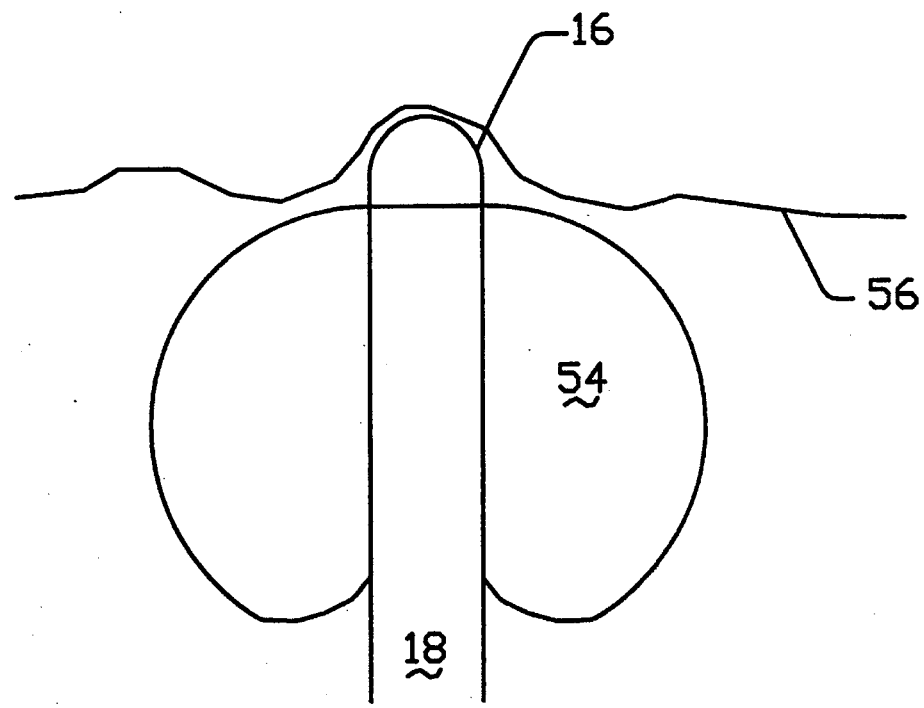
FIG. 4 is a cross-section through a third embodiment wherein the transducer means protrudes outside an inflatable balloon.

FIG. 4 shows the invention in a third embodiment in which catheter tip 16 protrudes ½ mm beyond the outside surface of an inflatable surrounding balloon 54. This geometry assists in imaging a myocardial surface 56 and in preventing penetration of such surfaces.

Figure 5:
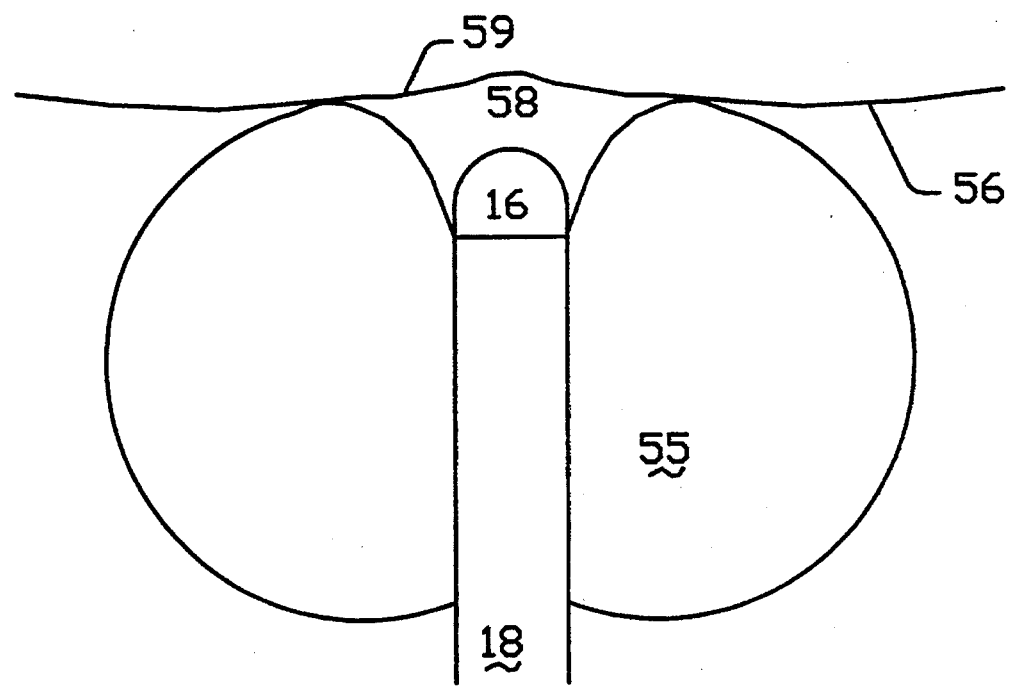
FIG. 5 is a cross-section through a fourth embodiment like FIG. 4 except the transducer means is recessed inside an inflatable balloon.

FIG. 5 shows a fourth embodiment with catheter tip 16 recessed ½ mm inside the surface of an inflated surrounding balloon 55. This recess dimple 58 traps blood to provide a coupling interface to wall 59.

Figure 6:
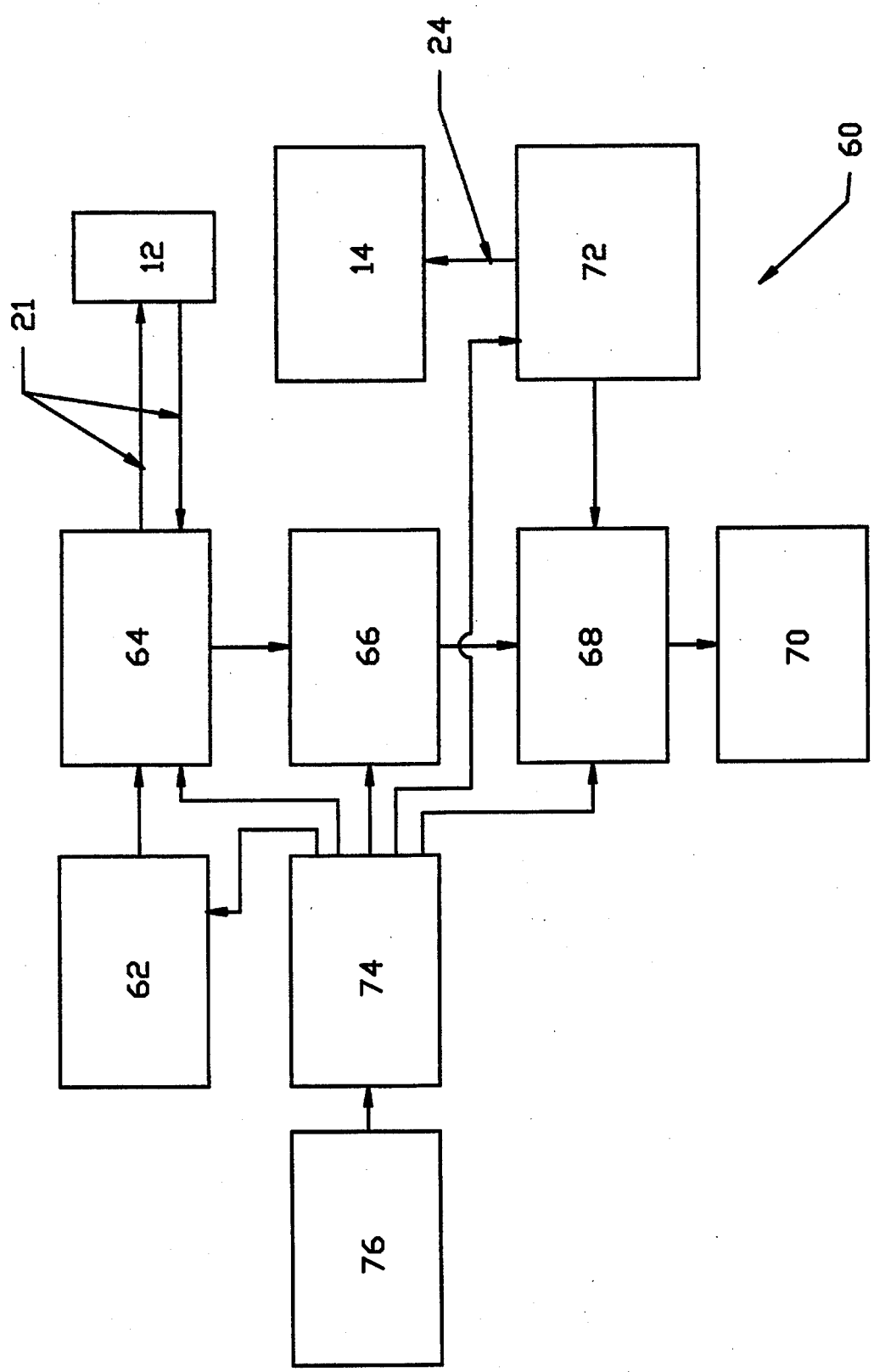
FIG. 6 is a schematic block diagram of a controller system for transmitting and receiving signals for an ultrasound microscope according to the invention.

FIG. 6 shows an electronic controller system 60 preferred for operating an ultrasonic microscope 10 of the present invention. A transmit signal generator 62 creates either an impulsive or short sinusoidal electrical pulse of a voltage suitable to drive piezoelectric transducer 12 for transmitting ultrasonic energy into surrounding tissue. During transmission, transmitter 62 is connected through a transmit/receive (T/R) switch 64 to the signal connection 21 of transducer 12, which is located inside catheter tube 18. Electricity drives piezoelectric transducer 12 to transmit ultrasonic energy into the tissue. The ultrasonic pulse transmission is immediately followed as the T/R switch 64 is placed into receive mode. Ultrasonic energy backscattered and impinging on transducer 12 is converted into electrical energy, passed through the T/R switch and applied to a receiver 66. Receiver 66 amplifies, filters, time gain compensates optionally to correct tissue attenuation effects, and envelope detects to generate signals representative of tissue backscattering.

The receiver 66 signal output is input to a scan converter 68. Then Input data is taken at arbitrary scanning geometries and generates an image for storage in a scan converter memory (not shown). The scan converter memory is read out for display for example on a standard raster scan CRT 70. Scan converter 68 and linear actuator drive means 72 are time-coordinated so that received data is stored in the proper scan converter 68 memory locations. Linear actuator drive means 72 generates electrical drive signals for moving transducer 14 synchronously with storing data in the scan converter memory. Overall system operation is controlled by system control processor 74, which also accepts user commands from an input device 76 such as a keyboard.

The present invention is described in terms of the preferred embodiments which may be modified without departing from the spirit of the invention. While the invention is presented as a cardiac catheter microscope, with suitable modifications it could be adapted for use in a hysteroscope, colonoscope, gastroscope, bronchoscope, laparoscope or surface imaging ultrasonic microscope. It is intended that the following claims be interpreted as having scopes covering modifications within the spirit of the invention.

We claim:

1. Ultrasound microscope means comprising:

delivery means having a body with inside and outside surfaces, a distal tip, and a lengthwise axis;

pivot means, secured to said tip, for mounting a transducer means pivotally around a pivot axis normal to said lengthwise axis;

ultrasound transducer means, mounted on said pivot means and positionable on a surface of in-vivo tissue to be imaged, for transmitting and receiving ultrasound containing frequency components in a bandwidth centered at approximately 200 MHz in beams to create A-scan lines forming an imaging surface which includes said lengthwise axis; and actuator means disposed at a first position for reciprocating said transducer means to scan ultrasound beams at angles to create a B-scan sector lying on said imaging surface;

conductor means for providing electrical signal connections to said transducer means and to said actuator means, disposed inside said delivery means; and controller means for controlling electrical signals flowing through respective conductor means to said transducer means and to said actuator means.

2. Ultrasound microscope means as recited in claim 1 and comprising:

acoustically transparent window means disposed on said distal tip, and coupling medium means for transmitting ultrasound between said transducer means and said window means.

3. Ultrasound microscope means as in claim 2 wherein said pivot means comprises a peripheral hinge.

4. Ultrasound microscope means as in claim 3 wherein said conductor means for said transducer comprises coaxial cable.

5. Ultrasound microscope means as in claim 4 wherein said transducer assembly comprises a polyvinylidene fluoride transducer and film metallizations on both sides of said transducer, and a backing and support means.

6. Ultrasound microscope means as recited in claim 2 wherein said pivot means comprises a ball joint disposed on said lengthwise axis.

7. Ultrasound microscope means as recited in claim 6 wherein said conductor means for said transducer means comprises a twisted pair.

8. Ultrasound microscope means as recited in claim 6 and further comprising a second actuator means disposed at a second position to scan sectors at any angle.

9. Ultrasound microscope means as recited in claim 1 wherein said actuator means comprises a piezoelectric bimorph.

10. Ultrasound microscope means as recited in claim 2 and further comprising an inflatable balloon disposed around said distal tip for positioning of said tip in a depression of an irregular surface of in-vivo tissue, and for preventing penetration of said tip into the surface of said in-vivo tissue to be imaged.

11. Ultrasound microscope means as recited in claim 10 wherein said balloon protrudes beyond said distal tip and forms a seal to trap body fluids between said surface and said tip.

12. Ultrasound microscope means as recited in claim 10 wherein said balloon recedes inside said distal tip.

13. Ultrasound microscope means as recited in claim 1 comprising controller means including:

a control signal generator for supplying control signals to said actuator means;

transmitter means for generating electrical energy;

electrical conductor means for conducting control signals to and from said transducer and actuator means;

receiver means for amplifying electrical signals generated by backscattered ultrasound energy received through said transducer means;

switch means for connecting said transducer means to said transmitter means during transmission or alternately to said receiver means during reception;

pixel-data storage means;

pixel data converter means to convert pixel data to output display data;

display means responsive to display data; and coordination means for synchronizing said transmitter means, actuator means, switch means, receiver means, pixel data storage and converter means, and display means.

14. Ultrasound microscope means as in claim 1 wherein said frequency components are within a bandwidth of approximately 200 MHz.

15. Ultrasound microscope means as in claim 14 wherein said frequency components are within a bandwidth of approximately 100 MHz.

* * * * *